United States Patent [19]

Arai et al.

[11] Patent Number: 4,604,347

[45] Date of Patent: Aug. 5, 1986

[54] ANALYTICAL ELEMENT FOR DRY ANALYSIS

[75] Inventors: Fuminori Arai; Mitsutoshi Tanaka; Harumi Katsuyama, all of Asaka, Japan

[73] Assignee: Fuji Photo Film Co., Ltd., Kanagawa, Japan

[21] Appl. No.: 577,090

[22] Filed: Feb. 6, 1984

[30] Foreign Application Priority Data

Feb. 7, 1983 [JP] Japan ................................. 58-17542

[51] Int. Cl.[4] ...................... C12Q 1/00; G01N 33/52
[52] U.S. Cl. ......................................... 435/4; 422/56; 422/57; 435/14; 435/22; 435/26; 435/805
[58] Field of Search ..................... 422/55–58; 435/805, 14, 22, 26, 4; 436/169, 170, 163, 97, 903

[56] References Cited

U.S. PATENT DOCUMENTS

| 4,132,528 | 1/1979 | Eikenberry et al. ............. 422/57 X |
| 4,153,668 | 5/1979 | Hill et al. ......................... 422/57 X |
| 4,258,001 | 3/1981 | Pierce et al. ......................... 422/56 |
| 4,435,362 | 3/1984 | Katsuyama et al. ................. 422/56 |

*Primary Examiner*—Arnold Turk
*Attorney, Agent, or Firm*—Toren, McGeady, Stanger, Goldberg & Kiel

[57] ABSTRACT

An analytical element containing at least one reagent for dry analysis of analyte in a liquid sample, which contains a nondiffusive acid and a nondiffusive base in different phases, being capable of adjusting the surrounding pH of the reaction area of at least one reagent under fluid contact therebetween, and said at least one reagent is contained in said nondiffusive acid-containing phase or nondiffusive base-containing phase.

10 Claims, No Drawings

ANALYTICAL ELEMENT FOR DRY ANALYSIS

BACKGROUND OF THE INVENTION

1. Field of the Invention

The present invention relates to an analytical element for dry analysis, and more particularly to an analytical element appropriately employable for dry analysis operation of substance contained in a body fluid in micro-quantity.

2. Description of Prior Arts

As a method of analysis of substance contained in a liquid sample such as a body fluid in a micro-quantity, there has been conventionally utilized a wet analysis such as a method comprising steps of bringing said substance into contact with other substance contained in a solvent so as to undergo a detectable reaction such as a reaction directly or indirectly producing or changing color, and detecting said reaction.

However, a dry analysis (i.e., dry analysis operation) developed for the purpose of simplifying the analytical procedures has been recently utilized. As a representative example of the analytical element utilized for the dry analysis, well known is a dry analytical element (also called a dry analytical material or article) which is in the form of a sheet, film, strip or tape basically comprising at least one reagent layer containing a reagent which directly or indirectly undergoes detectable reaction in contact with the substance under analysis (analyte), and a support thereof. The analysis employing the analytical element is generally carried out by procedures of applying a liquid sample containing the analyte onto the analytical element, subjecting the analytical element to incubation if necessary, measuring thus produced detectable reaction such as generation or change of color by means of a photometry or the like, and determining the amount of analyte according to colorimetry.

There are known a variety of analytical systems utilized in analysis of analyte employing the analytical element. Representative examples of the analytical system are as follows.

(A) An analytical system for detecting and measuring a detectable reaction between a reagent contained in a reagent layer and an analyte, such as generation or change of color. This analytical system is employed for analyses of analytes such as a variety of proteins, for instance, total protein, albumin and globulin, hemoglobin decomposition substances, for instance, free (nonconjugated or indirect) bilirubin and conjugated (direct) bilirubin.

(B) An analytical system employing a reagent layer containing at least two kinds of reagents, which comprises procedures of reacting one of the reagent with the analyte to produce a reactive substance such as ammonia or hydrogen peroxide, subsequently reacting the reactive substance with other reagent (e.g. dye precursor) in contact therebetween to cause a detectable reaction such as generation or change of color, and detecting and measuring the reaction. This analytical system is employable for analysis where analyte is glucose; lipids such as cholesterol, triglyceride and free fatty acid; enzymes such as lactate dehydrogenase; urea and uric acid.

(C) An analytical system employing a reagent layer containing a non-diffusive reagent having a color-forming group, which comprises procedures of converting the reagent into a diffusive product carrying the color-forming group by reaction with analyte, separating the diffusive product from the unreacted non-diffusive reagent, causing a detectable reaction such as generation or change of color in contact between the diffusive product and a chromogen substance such as coupler, and detecting and measuring the reaction. This analytical system is employable for analysis of polysaccharide hydrolase such as amylase.

(D) An analytical system employing a reagent layer containing a non-diffusive reagent having a detectable property (e.g., color), which comprises procedures of producing a diffusive product carrying the detectable property from the reagent by reaction with analyte, separating the diffusive product from the unreacted non-diffusive reagent, and detecting and measuring the diffusive product. This analytical system is employable for analysis of polysaccharide hydrolase such as amylase.

As described above, the analytical element contains a reagent reactive to analyte and may further contain another reagent reactive to a product produced by the reaction between the analyte and the former reagent. These reagents are selected appropriately to meet the purposes of the analysis. Among these reagents, not a few kind of reagents easily deteriorate under unsuitable surrounding pH conditions, or require specific pH conditions to show their reactivities. Accordingly, these reagents should be used under consideration on adjustment of their surrounding pH conditions.

For instance, a number of analytical detection systems using the dry analytical elements utilize enzymic reactions, in which the enzyme is an analyte, or is utilized as a reagent to decompose the analyte. The enzymic reaction generally proceeds smoothly in a pH range specifically adjusted to meet the requirement of the utilized enzyme. For this reason, the conventional dry analytical element is prepared to provide an optimum pH value for the enzyme to be utilized to the area (surroundings) where the predetermined enzymic reaction takes place. More in detail, the analytical element utilizing an enzyme as analyte contains a buffer reagent (known as a buffer reagent in the wet analysis) within a layer where the enzymic reaction is to take place, for instance, a layer containing a substrate of the enzyme. Otherwise, the analytical element utilizing an enzyme as a reagent for decomposing an analyte contains the buffer reagent within, for instance, a layer containing the enzyme. Thus, the conventional analytical element is adjusted on the surrounding pH conditions so as to allow smooth progress of the enzymic reaction.

In the analytical detection system, a detection system where the enzymic reaction product per se shows a color formation indicative of the amount of the analyte is known. Also generally known is a detection system where a reactive product produced by an enzymic reaction such as hydrogen peroxide reacts with a color-forming reagent (e.g., dye precursor) contained in the element to show color formation or color change. As the dye precursor, an azo-dye precursor such as a diazonium salt is known. The diazonium salt, however, has a problem that it is poor in preservability under the optimum surrounding pH conditions of most enzymes (pH range most preferable for the enzymic reaction). This means that: if the surrounding pH condition within the analytical element is set to meet the conditions appropriate for the enzymic reaction, the diazonium salt contained in the element decomposes or deteriorates in the course of storage of the element, while if the surrounding pH condition is set to meet the condition appropriate for preservation of the diazonium salt, the enzymic reaction utilized for the detection hardly proceeds smoothly.

For complying with the above-mentioned problem, it can be proposed that a diazonium-containing layer and a layer where the enzymic reaction is performed be independently arranged in the analytical element to incorporate a buffer reagent into only the latter enzymic reaction layer. However, even in this arrangement, a low molecuar weight buffer reagent permeates and diffuses from the enzymic reaction layer into the former diazonium-containing layer in the course of storage of the element. Accordingly, the decomposition or deterioration of the diazonium salt still occurs. The former diazonium-containing layer and the latter enzymic reaction layer should be brought into fluid contact (i.e., contact via fluid) with each other when the analytical operation is carried out. For this reason, these two layers cannot be arranged under complete separation.

A further problem is as follows. A reagent layer of a conventional analytical element utilizing an oxidase is prepared using a coating solution containing oxidase and a reduction-type leuco dye. In this example, the problem is: if the pH condition of the coating solution is adjusted to correspond to the optimum pH condition of the oxidase, the leuco dye is partially oxidized through oxidation reaction caused by oxygen in air in the course of preparation or storage of the analytical element. Accordingly, the leuco dye is liable to show color prior to performing analysis, resulting in reduction of the analytical accuracy.

As described above, the conventional analytical element hardly gives satisfactorily accurate results, as far as such detection system that there is observed difference between the optimum pH range for preservation of one or more reagent contained in the element and the optimum pH range for performing the detection reaction in the analytical operation is concerned. This problem is hardly solved, so far as the conventional buffer reagent is employed. For the same reason, two or more reagents having optimum pH ranges for preservation not being overlapped with each other are hardly contained in one analytical element.

SUMMARY OF THE INVENTION

The present inventors have discovered that the analytical element can be prepared to give a locally pH adjusted area within the analytical element by introducing a nondiffusive acid, preferably an acidic polymer, and a nondiffusive base, preferably a basic polymer, into the element, and that the introduction of the nondiffusive acid and base is able to appropriately adjust the pH condition at the time of performing the analytical operation.

Accordingly, the present invention provides an analytical element containing at least one reagent for dry analysis of analyte in a liquid sample, which contains a nondiffusive acid and a nondiffusive base in separate phases, being capable of adjusting the surrounding pH of the reaction area of at least one reagent under fluid contact therebetween, and said at least one reagent is contained in said nondiffusive acid-containing phase or nondiffusive base-containing phase.

DETAILED DESCRIPTION OF THE INVENTION

The dry analytical element (i.e., analytical element for dry analysis) of the present invention generally is in the form of a multilayer analytical element comprising a liquid-impermeable, light-transmissive support, one or more reagent layers, and a liquid sample-spreading layer (or simply a spreading layer) laminated in this order.

In the above-mentioned constitution, the support and liquid sample-spreading layer are known in their materials and constitutions. Accordingly, the support and liquid sample-spreading layer employable for constituting the multilayer analytical element according to the invention can be optionally formed utilizing these known materials and constitutions. If desired, one or more of functional layers known in the structures of the conventional dry analytical elements, for example, a light-reflecting layer, a light-blocking layer, a diffusion-preventing layer, and an adhesive layer (to be attached to the reagent layer) can be provided in the element.

If the laminated structure comprising the reagent layer and liquid sample-spreading layer is in the form of a self-supporting integrated sheet, the reagent layer and/or the liquid sample-spreading layer as such can serve as a support replacing the independent support. The liquid sample-spreading layer is not essential to the constitution of the analytical element of the present invention.

In the dry analytical element of the invention, the nondiffusive acid and nondiffusive base are placed in separate phases. The combination of the nondiffusive acid and bases preferably is a combination of an acidic polymer and a basic polymer placed in separate phases. The term "separate phases" generally means "separate layers".

The present invention is further described below, referring to an acidic polymer, namely, a preferable example of the nondiffusive acid, and a basic polymer, namely, a preferable example of the nondiffusive base.

The acidic polymer and basic polymer may form layers arranged separately from each other, or may be contained in layers provided separately from each other. Alternatively, one of the acidic polymer and basic polymer may be included in a layer of another polymer in the form of an encapsulated polymer phase. Thus, the phase may be in a form different from the layer.

According to the invention, at least one polymer selected from the acidic polymer and the basic polymer serves as a whole or a portion of a binder for retaining and fixing at least one reagent in the analytical element. Another polymer is generally provided in contact with a layer containing the above-mentioned polymer. However, the acidic polymer phase and basic polymer phase may be arranged not adjacent to each other, so long as these phases are arranged under fluid contact. The above-mentioned "another polymer" which is the acidic polymer or the basic polymer may contain at least one reagent participating in the reaction for detection of analyte, or may serve simply as a phase for adjusting pH condition in the aforementioned reagent-containing phase.

Examples of the construction of the dry analytical element of the present invention are given below, to illustrate representative arrangements of the acidic polymer phase and basic polymer phase.

(1) ANALYTICAL ELEMENT FOR ANALYSIS OF AMYLASE

Analytical element consisting essentially of the following layers laminated in the order:
(a) Support layer;
(b) Basic polymer layer (layer composed of basic polymer and gelatin);
(c) Color reaction layer (layer containing diazonium salt and utilizing acidic polymer as binder);
(d) Diffusion preventing layer;
(e) Coupler substrate layer (layer containing starch carrying color forming groups, i.e., coupler starch, serving as substrate); and
(f) Spreading layer.

(2) ANALYTICAL ELEMENT FOR ANALYSIS OF LDH (LACTATE DEHYDROGENASE)

Analytical element consisting essentially of the following layers laminated in the order:
(a) Support layer;
(b) Basic polymer layer (layer composed of basic polymer and gelatin);
(c) Reaction layer (layer containing lactic acid and tetrazolium salt and utilizing acidic polymer as binder); and
(d) Spreading layer.

(3) ANALYTICAL ELEMENT FOR ANALYSIS OF GLUCOSE

Analytical element consisting essentially of the following layers laminated in the order:
(a) Support layer;
(b) Basic polymer layer (layer composed of basic polymer, gelatin and hydrophobic polymer latex);
(c) Reaction layer (layer containing glucose oxidase, peroxidase, color-forming reagent, etc., and utilizing acidic polymer and gelatin both as binder); and
(d) Spreading layer.

Examples of the acidic polymer and basic polymer utilizable in the present invention are described below.

Examples of the acidic polymer include a homopolymer and copolymer of an unsaturated monomer selected from the group consisting of p-styrenesulfonic acid, acrylic acid, methacrylic acid, maleic acid, maleic anhydride, maleic monoamide, a monoester of maleic acid, N-(sulfoalkyl)acrylamide (preferably, N-(β-sulfo-t-butyl)acylamide, etc.), and N-(sulfoalkyl)methacrylamide (preferably, N-(β-sulfo-t-butyl)methacylamide, etc.), or a copolymer of the unsaturated monomer with other unsaturated monomer or monomers.

Examples of the basic polymer include a homopolymer and copolymer of an unsaturated monomer selected from the group consisting of 2-vinylpyridine, 4-vinylpyridine, N-vinylimidazole, 1-vinyl-3-alkyl-2,3-dihydroimidazole (i.e., 1-vinyl-3-alkyl-4-imidazoline, preferably 1-vinyl-3-ethyl-2,3-dihydroimidazole, 1-vinyl-3-methyl-2,3-dihydroimidazole, 1-vinyl-3-benzyl-2,3-dihydroimidazole, etc.), 2-vinyl-1-alkylimidazole, (preferably 2-vinyl-1-methylimidazole, 2-vinyl-1-benzylimidazole, etc.), (dialkylamino)alkylacrylate (preferably β-(dimethylamino)methylacrylate, β-(dimethylamino)ethylacrylate, β-(diethylamino)ethylacrylate, β-morpholinoethylacrylate, γ-(dimethylamino)propylacrylate, etc.), (dialkylamino)alkylmethacrylate (preferably β-(dimethylamino)methylmethacrylate, β-(dimethylamino)ethylmethacrylate, β-(diethylamino)ethylmethacrylate, β-morpholinoethylmethacrylate, γ-(dimethylamino)propylmethacrylate, etc.), N-[(dialkylamino)alkyl]acrylamide (preferably N-[(dimethylamino)propyl]acrylamide, etc.), and N-[(dialkylamino)alkyl]methacrylamide (preferably N-[(dimethylamino)propyl]methacrylamide, etc.), or a copolymer of the unsaturated monomer with other unsaturated monomer or monomers.

Examples of the "other unsaturated monomer" given above for the acidic and basic polymers include styrene, divinylbenzene, acrylamide, N-substituted acrylamide, methacrylamide, N-substituted methacrylamide, acrylic acid ester, methacrylic acid ester, and N-vinylpyrrolidone.

Either of the acidic polymer and basic polymer may be employed singly or in combination, and further may be employed in combination with other polymers, for example, water-soluble polymer or polymers such as gelatin and polyvinyl alcohol or aqueous latex of hydrophobic polymer or polymers.

The acidic polymer phase and basic polymer phase according to the present invention serve for adjusting the surrounding pH of the reaction area of at least one reagent under fluid contact between them. More in detail, when a liquid sample is introduced into the analytical element, the acidic polymer phase and basic polymer phase contact and interact with each other through the liquid to provide a buffer function.

Since the acidic polymer and basic polymer both have high molecular weights, these polymers hardly move in the analytical element. Thus, the unfavorable uniformisation of the surrounding pH condition within the conventional analytical element caused by the diffusion or movement of a low molecular weight buffer reagent (pH adjusting reagent) is effectively prevented in the present invention. That is, the desired adjustment of local surrounding pH condition as well as the desired adjustment of the reaction pH condition at the time of the analytical operation can be easily done by the introduction of the combination of acidic polymer and basic polymer into the analytical element according to the present invention. Accordingly, provision of pH condition appropriate for preservation of a diazonium salt and provision of pH condition appropriate for enzymic activity of amylase can be simulatenously accomplished, whereby an analytical element for highly accurate analysis of amylase can be prepared. Such analytical element for analysis of amylase with high accuracy has not been prepared by the prior arts.

The combination of the nondiffusive acidic and basic polymers, such as a combination of an acidic polymer and a basic polymer according to the present invention can be also utilized for adjustment of pH conditions of other analytical elements suffering similar drawbacks. Accordingly, the constitution of the present invention is effective for facilitating the preparation of the favorable analytical element as well as for enhancing the analytical accuracy in the use of the analytical element.

The following examples will further describe the present invention.

EXAMPLE 1

An analytical element for determination of amylase activity was prepared to have a structure of a support, a basic polymer layer, a color reaction layer containing acidic polymer, a diffusion-preventing layer, a coupler substrate layer, and a liquid sample-spreading layer (spreading layer) laminated in this order, using materials and coating solutions shown below.

(1) Support

A transparent polyethylene terephthalate (PET) film (thickness: 180 μm) provided with a gelatin subbing layer.

(2) Basic Polymer Layer

| Formulation of basic polymer layer | |
|---|---|
| Alkaline-treated gelatin | 2 g. |
| Poly(N—vinylimidazole) | 5 g. |
| Water | 60 g. |
| Polyoxyethylene nonylphenyl ether (containing 10 oxyethylene groups in one molecule on average) | 0.2 g. |

The formulated coating solution was coated over a support and then dried to form a basic polymer layer (thickness: 18 μm).

(3) Color Reaction Layer (i) Preparation of coating solution for the formation of color reaction layer To 100 ml. of water were added 5 g. of an acidic polymer (methyl vinyl ether-maleic anhydride copolymer, molar ratio 1:1, GANTREZ AN 139, trade name of GAF, inherent viscosity $[\eta] = 1.0$–$1.4$) and 1 g. of polyoxyethylene nonylphenyl ether (containing 10 oxyethylene groups in one molecule on average). The mixture was heated to 80° C. for 30 min. to perform esterification reaction. Thus a binder solution was prepared.

Independently, in a mixed medium consisting of 2 ml. of acetone and 4 ml. of ethyl alcohol was dissolved 0.150 g. of 2-methoxy-5-tetradecyloxycarbonylbenzenediazonium tetrafluoroborate to prepare a diazonium salt solution. Thus prepared solution was added to the above-described reaction liquid (binder solution) under stirring. After the addition was complete, the resulting liquid (coating solution for formation of color reaction layer) was kept under observation for 20 min. The liquid remained in the form of a transparent solution.

(ii) Formation of color reaction layer

On the basic polymer layer was coated the coating solution prepared in the above-described procedure, and then dried at 50° C. by air to form a color reaction layer containing acidic polymer having a dry thickness of 3 μm. Thus prepared dry color reaction layer showed high transparency.

(4) Diffusion-Preventing Layer

A mixture of 50 ml. of water, 80 g. of titanium dioxide fine powder and 0.5 g. of p-nonylphenoxypolyglycidol containing about 10 glycidol units (25% aqueous solution) was sufficiently pulverized in a ball mill-type pulverizer. To the pulverized mixture was added 300 g. of 3% aqueous agarose solution. The mixture was coated on the color reaction layer and dried to form a diffusion-preventing layer. Thus obtained diffusion-preventing layer had a thickness of 6 μm after dryness.

(5) Formation of Coupler Substrate Layer

A slurry was prepared by mixing 10 g. of the coupler starch (number of reactive coupler molecules/number of glucose units = 1/30) in which the reactive coupler was 2-[8-hydroxy-3,6-bis(sodium sulfonato)-1-naphthylamino]-4,6-dichloro-s-triazine prepared from cynauric chloride and 1-amino-8-hydroxynaphthalene-3,6-disulfonic acid monosodium salt according to a method described by J. T. Thurstton et al., in J. Amer. Chem. Soc., 73(7), 2981-29(1951), 105 g. of water, 80 g. of polyacrylamide (5% aqueous solution) and 2 g. of the p-nonylphenoxypolyglycidol (25% aqueous solution). The slurry was filtered over a nylon-mesh sheet filter to prepare a coating solution for forming the coupler substrate layer. Thus prepared solution was coated and dried on the diffusion-preventing layer to form the coupler substrate layer having a thickness of 10 μm (after dryness).

(6) Provision of Spreading Layer

A mix-spinned fabric of polyester (polyethylene terephthalate) and cotton (mixed rate: polyester/cotton = 75/25) was impregnated with an aqueous solution consisting of 150 g. of polyacrylamide (mean polymerization degree: 18,000, 0.8% aqueous solution) and 1 g. of p-nonylphenoxypolyglycidol (25% aqueous solution) to prepare a hydrophilic fabric.

A surface of the coupler substrate layer prepared as above was wetted with p-nonylphenoxypolyglicidol (0.2% aqueous solution), and then the hydrophilic fabric was laminated on the surface of the coupler substrate layer under pressure, and finally dried.

COMPARISON EXAMPLE 1

An analytical element for determination of amylase activity was prepared in the same manner as in Example 1 except that the basic polymer layer was not provided.

Evaluation of Analytical Element for Determination of Amylase Activity (1) Measurement of pH in coupler substrate layer upon introduction of liquid sample On the surface of the coupler substrate layer of the analytical element of Example 1 or Comparison Example 1 in each of which the spreading layer was not provided was spotted 10 μl. of human blood plasma. After 2 min., pH value of the substrate layer was measured by means of a surface electrode (GS-165F manufactured by Toa Denpa Co., Ltd., Japan). The results are set forth in Table 1.

TABLE 1

| pH Value of Coupler Substrate Layer | |
|---|---|
| Example 1 | Comparison Example 1 |
| pH 6.8 | 5.0 |

The results set forth in Table 1 indicate that the coupler substrate layer of the analytical element having the basic polymer layer (Example 1) showed a pH value maintained in the optimum pH range of amylase (pH 6.8–7.0) upon receiving a liquid sample, while the coupler substrate layer of the analytical element having no basic polymer layer (Comparison Example 1) showed a pH value apparently deviated from the optimum range.

(2) Determination of Amylase Activity

Fresh human saliva was diluted with a 7% albumin physiological saline solution to prepare an amylase standard liquid having activity value of 6,000 U/l. 10 μl. of the amylase standard liquid was spotted onto each spreading layer of the above-mentioned two analytical element to perform hydrolysis reaction at 37° C. The hydrolysis reaction was observed by measuring reflection optical density of the color reaction layer of the analytical element using a Macbeth Reflection Densitometer. The results are set forth in Table 2.

TABLE 2

Reflection Optical Density of Color Reaction
Layer (Wavelength for Measurement 560 nm)

| Reaction Period (min.) | Example 1 | Com. Example 1 |
|---|---|---|
| 1 | 0.10 | 0.03 |
| 2 | 0.23 | 0.09 |
| 3 | 0.34 | 0.18 |
| 4 | 0.46 | 0.23 |
| 5 | 0.57 | 0.31 |

The results set forth in Table 2 indicate that the sensitivity to the color reaction in the analytical element having the basic polymer layer was twice as high as that of the analytical element having no basic polymer layer.

EXAMPLE 2

An analytical element for determination of lactate dehydrogenase (LDH) activity was prepared to have a structure of a support, a basic polymer layer, a color reaction layer containing acidic polymer, and a spreading layer laminated in this order, using materials and coating solutions shown below.

(1) Support

A transparent PET film (thickness: 180 μm) provided with a gelatin subbing layer.

(2) Basic Polymer Layer

The same basic polymer layer as described in Example 1 was formed on the support.

(3) Color Reaction Layer (i) Formulation of coating solution of formation of color reaction layer

| | |
|---|---|
| NAD | 100 mg. |
| Lactic acid | 2 g. |
| Diaphorase | 20 U |
| 3, 3'-(3,3'-Dimethoxy-4,4'-biphenylylene)bis-[2-(p-nitrophenyl)-5-phenyl-2H—tetrazolium chloride] (2% methanol solution) | 5 ml. |
| Agarose Seaplaque (trademark of Marine Colloide Corp.) | 5 g. |
| Aqueous methyl vinyl etner - maleic acid copolymer solution (10% by weight, viscosity 300 cps) | 2.0 ml. |
| Polyoxyethylene nonylphenyl ether (containing 10 oxyethylene groups in one molecule on average) | 0.5 g. |

(ii) Formation of color reaction layer

On the basic polymer layer was coated the above-mentioned coating solution for the preparation of color reaction layer, and then dried at 50° C. by air to form a color reaction layer containing acidic polymer (thickness after dryness: 5 μm). Thus prepared dry color reaction layer showed high transparency.

(4) Spreading Layer

The surface of the color reaction layer prepared as above was wetted with water, and a membrane filter (mean pore size: 3.0 μm, thickness: 180 μm, FM-300, manufactured by Fuji Photo Film Co., Ltd., Japan) was laminated on the wetted surface to prepare the desired analytical element for determination of LDH activity.

COMPARISON EXAMPLE 2

An analytical element for determination of LDH activity was prepared in the same manner as in Example 2 except that the basic polymer layer was not provided and that the formulation of the coating solution for the formation of color reaction layer was replaced with the following formulation containing a conventional buffer solution in place of the acidic polymer.

| Formulation of color reaction layer | |
|---|---|
| NAD | 100 mg. |
| Lactic acid | 2 g. |
| Diaphorase | 20 U |
| 3, 3'-(3,3'-Dimethoxy-4,4'-biphenylylene)bis-[2-(p-nitrophenyl)-5-phenyl-2H—tetrazolium chloride] (2% methanol solution) | 5 ml. |
| Agarose Seaplaque (trademark of Marine Colloide Corp.) | 5 g. |
| Tris buffer solution | 0.12 M |
| Polyoxyethylene nonylphenyl ether (containing 10 oxyethylene groups in one molecule on average) | 0.5 g. |

(Remark: the amount of the tris buffer solution is given per the total amount of the coating solution)

COMPARISON EXAMPLE 3

An analytical element for determination of LDH activity was prepared in the same manner as in Example 2 except that the basic polymer layer was not provided.

Evaluation of Analytical Element for Determination of LDH Activity (1) Measurement of pH in color reaction layer upon introduction of liquid sample On a surface of the color reaction layer of the analytical element of Example 2 or Comparison Example 2 or 3 in each of which the spreading layer was not provided was spotted 10 μl. of human blood plasma. After 2 min., pH value of the color reaction layer was measured by means of a surface electrode (GS-165F manufactured by Toa Denpa Co., Ltd.). The results are set forth in Table 3.

TABLE 3

| | pH Value of Color Reaction Layer | | |
|---|---|---|---|
| | Example 2 | Com. Example 2 | Com. Example 3 |
| pH | 9.2 | 9.2 | 6.0 |

The results set forth in Table 3 indicate that the analytical element having the basic polymer layer (Example 2) showed a buffer action at a level similar to that of the analytical element containing a conventionally employed low molecular electrolyte in the color reaction layer (this element was known as having satisfactory buffer action). In contrast, the analytical element having no basic polymer layer (Comparison Example 3) showed a pH value apparently deviated from the optimum pH range of LDH (pH 9.0–10.0) upon receiving the liquid sample.

(2) Masurements of Background Fog (optical density observed in the absence of analyte) and Optical Density (i) Each of the analytical elements prepared in Example 2 and Comparison Examples 2, 3 was again prepared and immediately measured on the background fog by means of the Macbeth Reflection Densitometer.

Subsequently, 10 μl. of a control serum (Monitrol II, produced by Dade Corp.) was spotted on each analytical element and incubated at 37° C. for 10 min. Then, the color caused by the LDH in the serum was measured by means of the Macbeth Reflection Densitometer.

The results are set forth in Table 4.

TABLE 4

| | Reflection Optical Density of Color Reaction Layer (Wavelength for Measurement 530 nm) | | |
|---|---|---|---|
| | Example 2 | Com. Example 2 | Com. Example 3 |
| Background Fog | 0.16 | 0.32 | 0.15 |
| Color Density | 0.25 | 0.26 | 0.11 |

The results set forth in Table 4 indicate that the analytical element containing a conventional buffer reagent (Comparison Example 2) showed high background fog. This means that satisfactory accuracy could not be obtained by the use of such conventional analytical element.

(ii) Each of the analytical elements prepared in Example 2 and Comparison Examples 2, 3 was again prepared, allowed to stand at 25° C. for 10 days, and then measured on the background fog by means of the Macbeth Reflection Densitometer.

Subsequently, 10 μl. of a control serum (Monitrol II, produced by Dade Corp.) was spotted on each analytical element and incubated at 37° C. for 10 min. Then, the color caused by the LDH in the serum was measured by means of the Macbeth Reflection Densitometer.

The results are set forth in Table 5.

TABLE 5

| | Reflection Optical Density of Color Reaction Layer Wavelength for Measurement 530 nm) | | |
|---|---|---|---|
| | Example 2 | Com. Example 2 | Com. Example 3 |
| Background Fog | 0.17 | 0.45 | 0.16 |
| Color Density | 0.26 | 0.15 | 0.11 |

The results set forth in Table 5 indicate that the analytical element containing a conventional buffer reagent (Comparison Example 2) showed higher background fog further increased on storage. This means that satisfactory accuracy could not be obtained by the use of such conventional analytical element. The low color density shown in the use of the element of Comparison Example 2 is thought to be caused by oxidation of the tetrazolium salt contained as the color-forming reagent.

(3) Evaluation on buffer action of the analytical element of Example 2

On the surface of the color reaction layer of the analytical element of Example 2 in which the spreading layer was not provided was spotted 10 μl. of human blood plasma under varaiation of its pH value, for the purpose of evaluating function of the provision of the basic polymer layer. After 2 min., pH value of the color reaction layer was measured by means of a surface electrode (GS-165F manufactured by Toa Denpa Co., Ltd.). The results are set forth in Table 6.

TABLE 6

| pH Value of Color Reaction Layer | |
|---|---|
| pH of Sample Blood Plasma | pH of Color Reaction Layer |
| 7.4 | 8.9 |
| 7.6 | 8.9 |
| 7.9 | 9.0 |
| 8.2 | 9.1 |
| 8.4 | 9.1 |

The results set forth in Table 6 indicate that the analytical element according to the present invention showed satisfactory buffer action.

EXAMPLE 3

An analytical element for analysis of glucose was prepared to have a structure of a support, a basic polymer layer, a color reaction layer containing acidic polymer, and a spreading layer laminated in this order, using materials and coating solutions shown below.

(1) Support

A transparent polyethylene terephthalate (PET) film (thickness: 180 μm) provided with a gelatin subbing layer.

(2) Basic Polymer Layer (i) Formulation of coating solution for formation of basic polymer layer

| | |
|---|---|
| Aqueous gelatin solution (10%) | 20 ml. |
| Aqueous solution of divinylbenzene - N,N—diethyl-aminomethylstyrene copolymer (mole ratio 10:90, resin content 15%) | 6 ml. |

(ii) Formation of basic polymer layer

The above-mentioned coating solution was coated over a support and then dried to form a basic polymer layer (thickness: 5 μm).

(3) Color Reaction Layer (i) Formulation of color reaction layer

| | |
|---|---|
| Glucose oxidase | 20,000 U/m$^2$ |
| Peroxidase | 20,000 U/m$^2$ |
| 4-Aminoantipyrine | 1.5 g/m$^2$ |
| 1,7-Dihydroxynaphthalene | 0.7 g/m$^2$ |
| Alkaline-treated gelatin | 15 g/m$^2$ |
| Aqueous methyl vinyl ether - maleic acid copolymer solution (10% by weight, viscosity 300 cps) | 5 g/m$^2$ |
| Polyoxyethylene nonylphenyl ether (containing 10 oxyethylene groups in one molecule on average) | 0.2 g/m$^2$ |

(ii) Formation of color reaction layer

On the basic polymer layer was coated the above-mentioned coating solution for the preparation of color reaction layer, and then dried at 50° C. by air to form a color reaction layer containing acidic polymer (thickness after dryness: 5 μm). Thus prepared dry color reaction layer showed high transparency.

(4) Provision of Spreading Layer

The surface of the color reaction layer prepared as above was wetted with water, and a membrane filter (mean pore size: 3.0 μm, thickness: 180 μm, FM-300, manufactured by Fuji Photo Film Co., Ltd.) was laminated on the wetted surface to prepare the desired analytical element for analysis of glucose.

Evaluation of Analytical Element for Analysis of Glucose (1) Measurement of pH in color reaction layer upon introduction of liquid sample On the surface of the color reaction layer of the analytical element of Example 3 in which the spreading layer was not provided was spotted 10 μl. of human blood plasma. After 2 min., pH value of the color reaction layer was measured by means of a surface electrode (GS-165F manufactured by Toa Denpa Co., Ltd.). The measured value was pH 5.6, being identical to the optimum pH (approx. 5.6) of glucose oxidase.

(2) Analysis of Glucose

On the spreading layer of the analytical element of Example 3 was spotted 10 μl. of human blood plasma containing a certain amount of sodium fluoride, and the element was incubated at 37° C. for 10 min. Subsequently, the color formation caused by glucose in the plasma was measured. The results are set forth in Table 7.

TABLE 7

| Reflection Optical Density of Color Reaction Layer (Wavelength for Measurement 510 nm) | | | | |
|---|---|---|---|---|
| Content of Sodium Fluoride (mg/dl) | | | | |
| 0 | 2 | 5 | 10 | 20 |
| 0.49 | 0.49 | 0.50 | 0.49 | 0.50 |

The results set forth in Table 7 indicate that the color reaction occurring in the analytical element of the present invention is hardly disturbed by sodium fluoride (preservative for blood and serum sample) in a liquid sample.

We claim:

1. An analytical element for dry analysis of analyte in a liquid sample which contains a liquid-impermeable, light-transmissive support, a non-diffusive acid-containing layer, and a non-diffusive base-containing layer, the latter two layers being arranged on the support such that both layers upon liquid contact adjust the surrounding pH of a predetermined reaction area and wherein at least one of the latter two layers contains a reagent which participates in the analytical reaction which takes place.

2. The analytical element as claimed in claim 1 in which the non-diffusive acid-containing layer and the non-diffusive base-containing layer are arranged adjacently to each other.

3. The analytical element as claimed in claim 1 in which a liquid sample-spreading layer is provided in the outermost position from the support and the non-diffusive acid-containing layer and the non-diffusive base containing-layer are each sandwiched between the support and the liquid sample-spreading layer.

4. The analytical element as claimed in claim 1 which comprises a liquid sample-spreading layer, a non-diffusive acid-containing reaction layer which contains the reagent, a non-diffusive base-containing layer, and a support arranged in this order.

5. The analytical element as claimed in claim 1, 2, or 3, in which said nondiffusive acid and nondiffusive base are an acidic polymer and a basic polymer, respectively.

6. The analytical element as claimed in claim 1, 2, or 3, in which said acidic polymer is a homopolymer or copolymer of an unsaturated monomer selected from the group consisting of p-styrenesulfonic acid, acrylic acid, methacrylic acid, maleic acid, maleic anhydride, maleic monoamide, monoester of maleic acid, N-(sulfoalkyl)acrylamide and N-(sulfoalkyl)methacrylamide, or a copolymer of said unsaturated monomer with other unsaturated monomer or monomers.

7. The analytical element as claimed in claim 1, 2, or 3, in which said basic polymer is a homopolymer or copolymer of an unsaturated monomer selected from the group consisting of 2-vinylpyridine, 4-vinylpyridine, N-vinylimidazole, 1-vinyl-3-alkyl-2,3-dihydroimidazole, 2-vinyl-1-alkylimidazole, (dialkylamino)alkylacrylate, (dialkylamino)alkylmethacrylate, N-/(dialkylamino)alkyl/acrylamide and N-/(dialkylamino)alkyl/methacrylamide, or a copolymer of said unsaturated monomer with other unsaturated monomer or monomers.

8. The analytical element as claimed in claim 1, 2, or 3, in which said reagent contained in said nondiffusive acid-containing phase or nondiffusive base-containing phase is a color-forming reagent.

9. The analytical element as claimed in claim 8, in which the reagent is capable of reacting with an enzyme or a substrate of enzyme.

10. The analytical element as claimed in claim 8, in which said color-forming reagent is a diazonium salt.

* * * * *